United States Patent [19]
Yi Wang et al.

[11] Patent Number: 6,048,538
[45] Date of Patent: Apr. 11, 2000

[54] PEPTIDES DERIVED FROM THE NON-STRUCTURAL PROTEINS OF FOOT AND MOUTH DISEASE VIRUS AS DIAGNOSTIC REAGENTS

[75] Inventors: Chang Yi Wang, Cold Spring Harbor; Fan Shen, Bayside; Pei De Chen, Kew Gardens, all of N.Y.

[73] Assignee: United Biomedical, Inc., Hauppauge, N.Y.

[21] Appl. No.: 08/943,173

[22] Filed: Oct. 3, 1997

[51] Int. Cl.[7] .................... A61K 39/125; A61K 38/00; C12Q 1/70
[52] U.S. Cl. ................... 424/216.1; 424/184.1; 424/185.1; 424/186.1; 424/204.1; 435/5; 435/7.1; 435/69.3; 435/975; 530/300; 530/324; 530/326; 530/350; 530/826
[58] Field of Search ................... 530/300, 350, 530/324, 326, 826; 424/184.1, 185.1, 186.1, 204.1, 216.1; 435/5, 7.1, 69.3, 975

[56] References Cited

U.S. PATENT DOCUMENTS

4,732,971  3/1988  DiMarchi et al. ............... 530/324

FOREIGN PATENT DOCUMENTS

WO 83/03547  10/1983  WIPO .
WO 89/09228  10/1989  WIPO .
WO 91/03255  3/1991  WIPO .

OTHER PUBLICATIONS

C.A. Lobo Arias et al., (1976) "Antibody Response of Tropical Range Cattle to Foot–And–Mouth Disease Virus" *Int'l Symposium on Foot–and–Mouth Disease* 35:343–356.
James L. Bittle et al. (1982) "Protection Against Foot–and–Mouth Disease by Immunization with a Chemically Synthesized Peptide Predicted from the Viral Nucleotide Sequence" *Nature* 298:30–33.
Fred Brown (1992) "New Approaches to Vaccination against Foot–and–Mouth Disease" *Vaccine* 10:1022–1026.
S.J. Barteling et al. (1991) "Developments in Foot–and–Mouth Disease Vaccines" *Vaccine* 9:75–88.
J. Lubroth et al. (1995) "Identification of Native Foot–and–Mouth Disease Virus Non–Structural Protein 2C as a serological indicator to Differentiate Infected from Vacinated Livestock" *Res. Vet. Sci.* 59:70–78.
J. Lubroth et al. (1996) "Absence of Protein 2C from Calrified Foot–and–Mouth Disease Virus Vaccines Provides the Basis for Distinguishing Convalescent from Vaccinated Animals" *Vaccine* 14:419–427.
M.G. Mateu et al. (1989) "Implications of a Quasispecies Genome Structure: Effect of Frequent, Naturally Occurring Amino Acid Substitutions on the Antigenicity of Foot–and–Mouth Disease Virus" *Pro. Natl. Acad. Sci. USA* 86:5883–5887.
J.F.E. Newman et al. (1994) "Foot–and–Mouth Disease Virus Particles Contain Replicase Protein 3D" *Pro. Natl. Acad. Sci. USA* 91:733–737.

Ana Rodriguez et al. (1994) "Immunogenicity of Non–Structural Proteins of Foot–and–Mouth Disease Virus: Differences Between Infected and Vaccinated Swine" *Archives Virology* 136:123–131.
A.A. Pinto et al. (1979) "Immune Response to Virus–Infection–Associated (VIA) Antigen in Cattle Repeatedly Vaccinated with Foot–and–Mouth Disease Virus Inactivated by Formalin or Acetylethyleneimine" *Hyg., Comb.* 82:41–50.
Michael Tesar et al., (1989) "Serological Probes for Some Foot–and–Mouth Disease Virus Nonstructural Proteins", *Virus Genes,* 3:1, 29–44.
Erika Neitzert et al., (1991) "Expression of the Aphthovirus RNA Polymerase Gene in *Escherichia coli* and Its Use Together with Other Bioengineered Nonstructural Antigens in Detection of Late Persistent Infections" *J Virology,* 184:799–804.
Klaus Strebel et al., (1986) "Characterization of Foot–and–Mouth Disease Virus Gene Products with Antisera Against Bacterially Synthesized Fusion Proteins" *J Virology,* 57 (3):983–991.
C. Hamblin et al., (1986) "A new enzyme–linked immunosorbent assay (ELSA) for the detection of antibodies against foot–and–mouth virus" *Immunol Methods,* 93:115–121.
H.G. Berger et al., (1990) "Identification of foot–and–mouth disease virus replication in vaccinated cattle by antibodies to non–structural virus proteins" *Vaccine,* 8:213–216.
Ingrid E. Bergmann et al. (1993) "Diagnosis of persistent aphthovirus infection and its differentiation from vaccination response in cattle by use of enzyme–linked immunoelectrotransfer blot analysis with bioengineered nonstructural viral antigens" *Am. J. Vet Res,* 54 (6):825–831.
A. Alonso et al., (1990) "Detection of foot–and–mouth disease virus infection–associated antigen antibodies: comparison of the enzyme–linked immunosorbent assay and agar gel immunodiffusion tests" *Preventive Vet Med,* 9:233–240.
F. Villinger et al., (1989) "Antibodies to Foot–and–Mouth Disease Virus Infection Associated (VIA) Antigen: Use of Bioengineered VIA Protein as Antigen in an ELISA" *Vet Microbiology,* 20:235–246.

*Primary Examiner*—Donna Wortman
*Assistant Examiner*—Mary K. Zeman
*Attorney, Agent, or Firm*—Morgan & Finnegan, LLP

[57] ABSTRACT

The present invention is directed to novel peptides derived from the non-structural proteins of the Foot-and-mouth Disease Virus (FMDV) and their use for the detection in animal body fluids of antibodies to FMDV. The peptides of the invention are useful for the diagnosis of FMDV infection, detection of potential carrier status, and for the differentiation of infected from vaccinated animals. The amino acid sequence of each of the peptides of the present invention correspond to an immunodominant region of the non-structural proteins 3A, 3B and 3C of FMDV. More particularly, the present invention is directed to the use of a peptide selected from a group consisting SEQ ID NOS:4–16 or their analogs for the detection of antibodies to FMDV in animal body fluids. The detection method includes an enzyme-linked immunosorbent assay (ELISA), and other well-known immunoassay formats.

14 Claims, 6 Drawing Sheets

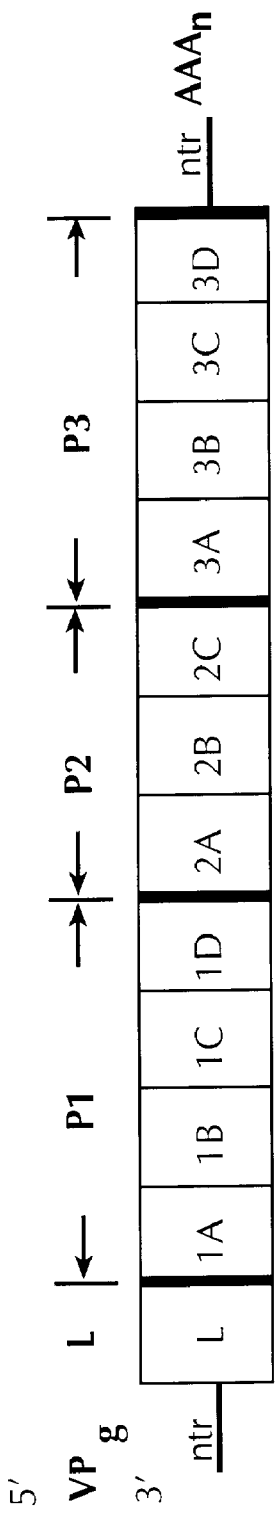

FIG. 3

```
  1  Gly-Pro-Tyr-Thr-Gly-Pro-Leu-Glu-Arg-Gln-Arg-Pro-leu-Lys-Val-
 16  Arg-Ala-Lys-Leu-Pro-Gln-Gln-Glu-Gly-Pro-Tyr-Ala-Gly-Pro-Leu-
 31  Glu-Arg-Gln-Lys-Pro-Leu-Lys-Val-Lys-Ala-Lys-Ala-Pro-Val-Val-
 46  Lys-Glu-Gly-Pro-Tyr-Glu-Gly-Pro-Val-Lys-Lys-Pro-Val-Ala-Leu-
 61  Lys-Val-Lys-Ala-Lys-Asn-Leu-Ile-Val-Thr-Glu
```

FIG. 4

```
  1  Ser-Gly-Ala-Pro-Pro-Thr-Asp-Leu-Gln-Lys-Met-Val-Met-Gly-Asn-
 16  Thr-Lys-Pro-Val-Glu-Leu-Ile-Leu-Asp-Gly-Lys-Thr-Val-Ala-Ile-
 31  Cys-Cys-Ala-Thr-Gly-Val-Phe-Gly-Thr-Ala-Tyr-Leu-Val-Pro-Arg-
 46  His-Leu-Phe-Ala-Glu-Leu-Tyr-Lys-Ile-Met-Leu-Asp-Gly-Arg-
 61  Ala-Met-Thr-Asp-Ser-Asp-Tyr-Arg-Val-Phe-Glu-Phe-Glu-Ile-Lys-
 76  Val-Lys-Gly-Gln-Asp-Met-Leu-Ser-Asp-Ala-Ala-Leu-Met-Val-Leu-
 91  His-Arg-Gly-Asn-Arg-Val-Arg-Asp-Ile-Thr-Lys-His-Phe-Arg-Asp-
106  Thr-Ala-Arg-Met-Lys-Gly-Thr-Pro-Val-Gly-Val-Val-Ala-Asn-
121  Asn-Ala-Asp-Val-Gly-Arg-Leu-Ile-Phe-Ser-Gly-Glu-Ala-Leu-Thr-
136  Tyr-Lys-Asp-Ile-Val-Cys-Met-Asp-Gly-Asp-Thr-Met-Pro-Ser-
151  Leu-Phe-Ala-Leu-Tyr-Lys-Ala-Thr-Lys-Ala-Gly-Tyr-Cys-Gly-Gly-
166  Ala-Val-Leu-Ala-Lys-Asp-Gly-Ala-Asp-Thr-Phe-Ile-Val-Gly-Thr-
181  His-Ser-Ala-Gly-Asn-Gly-Val-Gly-Tyr-Cys-Ser-Cys-Val-Ser-
196  Lys-Ser-Met-Leu-Leu-Arg-Met-Lys-Ala-His-Val-Asp-Pro-Glu-Pro-
211  Gln-His-Glu
```

FIG. 6B
(Day 11)
Taiwan 1997, O type
● Animal# 016 (infected)
▲ Animal# 019 (infected)

FIG. 6C
● Animal# 070 (Vaccinated)
▲ Animal# 071 (Vaccinated)

PEPTIDES DERIVED FROM THE NON-STRUCTURAL PROTEINS OF FOOT AND MOUTH DISEASE VIRUS AS DIAGNOSTIC REAGENTS

INTRODUCTION

The present invention is directed to novel peptides derived from the non-structural proteins of the Foot-and-mouth Disease Virus (FMDV) and their use for the detection of FMDV infection in animal body fluids. In particular, the peptides of the present invention are useful to diagnose FMDV infection, to determine the potential carrier status in an animal, and to differentiate infected from vaccinated animals. The amino acid sequences of these peptides correspond to immunodominant regions of the non-structural proteins 3A, 3B and 3C of FMDV. More specifically, the composition of peptides or their analogues of the present invention are useful for the detection of antibodies to FMDV in animal body fluids by immunoassay such as the enzyme-linked immunosorbent assay (ELISA), or other well-known immunoassay formats.

BACKGROUND OF THE INVENTION

Foot-and-mouth disease (FMD) is an economically devastating infectious disease of farm animals. Cattle, pigs, sheep and goats are all susceptible. The causative agent is FMDV, an aphthovirus of the Picornaviridae family for which seven serotypes have been described. The FMDV genome consists of a single RNA positive strand encoding four structural proteins (VP1–VP4) and, at least, ten non-structural polypeptides induced in infected cells. The non-structural proteins include a viral RNA replicase 3D (Newman et al., *Proc Natl Acad Sci USA,* 1994, 91:733), also termed FMDV infection associated antigen (VIAA). The coding region for structural and nonstructural proteins is shown schematically in FIG. 1.

Animal husbandry is a major industry which can be crippled by the spread of FMDV through the susceptible population. The presently available method for controlling the disease is by vaccination with a chemically inactivated viral composition. Despite the availability of the vaccine, it is very important when there is a outbreak of the disease to be able to identify rapidly the animals that have been infected to isolate them from the non-diseased animals. Moreover, it has been found that the infected but convalescent animals frequently become carriers of the virus. Such animals can become the source of new outbreaks of the disease and can introduce antigenic variants into a susceptible population. Because of this problem, a rapid serological method is needed to identify previously infected but convalescent and asymptomatic animals and distinguish them from vaccinated animals. Such a method would aid regional efforts to eliminate the virus through vaccination programs, and serve to facilitate international livestock trade even in the event of an outbreak of the disease.

The detection of VIAA (also known as 3D) by agar gel immunodiffusion or virus isolation have been used for years to identify infected animals. The low sensitivity of these methods makes them difficult for routine application. To overcome this problem, ELISA assays to detect specific antibodies against the whole virion (Hamblin et al., *J Immunol Methods,* 1986, 93:115), viral subunits (Smitsaart et al., *J Virol,* 1986, 57:983) or VIAA (Alonso et al., *Prev Vet Med,* 1990, 9:233) have been developed. The tests which detect the antibodies to the whole virus or to the structural proteins cannot distinguish between infected and vaccinated animals. The VIAA-based assays also failed to distinguish between infected and vaccinated animals because the infected cell culture extracts used in vaccines usually contain the 3D protein at a concentration sufficient to provoke antibodies against 3D (Pinto et al., *J Hyg Camb,* 1979, 82:41).

It has been reported that non-structural proteins 2B, 2C, 3AB, and 3ABC, produced in BHK cells infected with the virus, are precipitated by sera from convalescent animals, but only occasionally by those that have been vaccinated (Villiner et al., *Veterinary Microbiol,* 1989, 20:235; Tesar et al., *Vir Genes,* 1989, 3:29; Berger et al., *Vaccine,* 1990, 8:213; Neitzert et al., *Virology,* 1991, 184:799; Bergmann et al., *Am J Vet Res,* 1993, 54:825; Rodriguez et al., *Arch Virol,* 1994, 136:123; Lubroth et al., *Res Vet Sci,* 1995, 59:70). The use of 2C and 3ABC proteins have been proposed as potential candidates for the differential diagnosis of convalescent and vaccinated animals. However, 3ABC-derived polyproteins have proven to be unreliable for differential diagnosis (Lubroth et al., 1995). Moreover, the existing methods based on the detection of 2C and 3ABC proteins and polyproteins are expensive and cumbersome and impractical for routine assays. The assay methods, such as immunoprecipitation (Lubroth, et al., 1995); determinations of relative reactivities (i.e., ratios between different ELISA procedures); and immunoblots (Rodriguez et al., 1994) suffer from poor sensitivity and lack of specificity. It has also been proposed to use peptides derived from 2C and 3ABC in immunoassay. However, up to the present none have been reported.

Synthetic peptides have been used in the recent years to map antigenic or immunogenic sites on the surface of proteins, an approach also known as "site-directed-serology". This approach has been explored by one of the co-inventors (Wang, C. Y.) to identify and characterize highly antigenic epitopes on various viral proteins of HIV, HTLV and HCV and to develop sensitive and specific diagnostic immunoassay using peptides comprising these antigenic epitopes for HIV, HTLV and HCV (U.S. Pat. Nos. 4,735,896, 4,879,212, 4,833,071, 5,476,765, 5,106,726, 5,436,126). These assays have provided excellent sensitivity and specificity due to the high molar concentration of the reagent and the lack of unrelated bacterial, viral or host cell proteins. Further, in the case of HTLV-I and HTLV-II, the peptide-based immunoassay has provided an unmatched capability to differentiate between two closely related viruses. These peptide-based immunoassay overcame many of the existing problems associated with either viral lysates or recombinantly produced proteins.

The present invention employs novel FMDV nonstructural protein derived peptides and peptide compositions identified through site directed serology as immunoreagents. The method overcomes the deficiencies in sensitivity and specificity of the currently available FMDV-immunoassay. The immunoassays incorporate the peptides of the present invention for the capture of antibodies to Foot-and-mouth Disease Virus (FMDV) in animal body fluids and are useful for the diagnosis of FMDV infection, to identify potential carrier status, and to differentiate infected from vaccinated animals.

SUMMARY OF THE INVENTION

The present invention provides novel peptides derived from the non-structural proteins of FMDV which are specifically immunoreactive with these proteins and are useful for the diagnosis of FMDV infection.

A novel peptide of the present invention comprises an immunogenic epitope specific to antibodies of FMDV consisting of 15 to 75 amino acids in a sequence corresponding to a non-structural protein of a strain/isolate of FMDV selected from the group consisting of 3A, 3B and 3C, and analogs thereof wherein an amino acid is conservatively substituted, and optionally having 1–5 amino acids added to the terminal amino acid selected from the group consisting of lysine, methionine, glycine, and alanine. The novel peptide of the present invention is useful as an immunoreagent in an immunoassay method for the detection of FMDV infection.

Specifically, the present invention provides a peptide or a peptide composition comprising a peptide selected from the group consisting of SEQ ID NOS: 4 to 16 (see Tables 1 and 2) with specific immunoreactivity to antibodies to the non-structural proteins, 3A, 3B and 3C, of FMDV.

The peptide or the peptide composition of the present invention are useful as immunoreagents in a method for detecting antibodies to FMDV or diagnosis of FMDV infection, particularly as an reagent in an immunoassay. The present invention also provides test kits for the immunoassays for the detection and diagnosis of FMDV infection. The preferred immunoassay formats are ELISA and immunoagglutination.

It is an object of the present invention to provide a peptide derived from the non-structural proteins of FMDV for use in a method for the early identification and routine monitoring of FMDV infection.

Another object is to develop a highly sensitive and accurate method for the detection of FMDV infection and the determination of the carrier status of FMDV infected but convalescent and asymptomatic animals.

A further object is to develop a chemically synthesized test reagent which can be quality controlled and used as a routine test to detect the presence of antibodies to FMDV in body fluids and to differentiate between FMDV infected and vaccinated animals.

A further object is to develop a highly sensitive and accurate method capable of detecting FMDV infection in animals from diverse geographical regions with diverse serotypes of FMDV, e.g., SAT, C, O, A, Asia.

TABLE 1

Amino Acid Sequences of FMDV Nonstructural Protein Derived Peptides

FMDV 3A

| Peptide Code | Corresponding to Amino Acid Sequence of FIG. 2 |
| --- | --- |
| 2299 | AA136–153 |
| 2300 | AA124–141 (SEQ ID NO:4) |
| 2301 | AA112–129 (SEQ ID NO:5) |
| 2302 | AA104–117 |
| 2303 | AA 88–105 |
| 2304 | AA 76–93 (SEQ ID NO:6) |
| 2305 | AA 64–81 |
| 2306 | AA 52–69 |
| 2307 | AA 40–57 |
| 2308 | AA 27–45 |
| 2309 | AA 14–32 |
| 2310 | AA 1–19 |

FMDV 3B

| Peptide Code | Corresponding to Amino Acid Sequence of FIG. 3 |
| --- | --- |
| 2311 | AA 57–71 |
| 2312 | AA 40–58 (SEQ ID NO:7) |
| 2313 | AA 27–45 (SEQ ID NO:8) |
| 2314 | AA 14–32 (SEQ ID NO:9) |
| 2315 | AA 1–19 (SEQ ID NO:10) |

FMDV 3C

| Peptide Code | Corresponding to Amino Acid Sequence of FIG. 4 |
| --- | --- |
| 2316 | AA196–213 |
| 2317 | AA184–201 |
| 2318 | AA172–190 |
| 2319 | AA160–177 |
| 2320 | AA148–166 |
| 2321 | AA136–153 |
| 2322 | AA124–141 (SEQ ID NO:11) |
| 2323 | AA112–129 |
| 2324 | AA100–118 (SEQ ID NO:12) |
| 2325 | AA 88–105 |
| 2326 | AA 76–94 |
| 2327 | AA 64–81 |
| 2328 | AA 52–69 |
| 2329 | AA 40–57 |
| 2330 | AA 27–45 |
| 2331 | AA 14–32 |
| 2332 | AA 1–19 (SEQ ID NO:13) |

TABLE 2

Amino Acid Sequences of FMDV Nonstructural Protein Derived Antigenic Peptides Peptide 2374 (AA76-141 From 3A Protein)

| | |
|---|---|
| Ile-Arg-Glu-Thr-Arg-Lys-Arg-Gln-Lys-Met-Val-Asp- | 12 |
| Asp-Ala-Val-Asn-Glu-Tyr-Ile-Glu-Lys-Ala-Asn-Ile- | 24 |
| Thr-Thr-Asp-Asp-Thr-Thr-Leu-Asp-Glu-Ala-Glu-Lys- | 36 |
| Asn-Pro-Leu-Glu-Thr-Ser-Gly-Ala-Ser-Thr-Val-Gly- | 48 |
| Phe-Arg-Glu-Arg-Thr-Leu-Thr-Gly-Gln-Arg-Ala-Cys- | 60 |
| Asn-Asp-Val-Asn-Ser-Glu | 66 |
| | SEQ ID NO:14 |

Peptide 2373 (AA112-141 From 3A Protein)

| | |
|---|---|
| Asn-Pro-Leu-Glu-Thr-Ser-Gly-Ala-Ser-Thr-Val-Gly- | 12 |
| Phe-Arg-Glu-Arg-Thr-Leu-Thr-Gly-Gln-Arg-Ala-Cys- | 24 |
| Asn-Asp-Val-Asn-Ser-Glu | 30 |
| | SEQ ID NO:15 |

Peptide 2372 (AA1-58 From 3B Protein)

| | |
|---|---|
| Gly-Pro-Tyr-Thr-Gly-Pro-Leu-Glu-Arg-Gln-Arg-Pro- | 12 |
| Leu-Lys-Val-Arg-Ala-Lys-Leu-Pro-Gln-Gln-Glu-Gly- | 24 |
| Pro-Tyr-Ala-Gly-Pro-Leu-Glu-Arg-Gln-Lys-Pro-Leu- | 36 |
| Lys-Val-Lys-Ala-Lys-Ala-Pro-Val-Val-Lys-Glu-Gly- | 48 |
| Pro-Tyr-Glu-Gly-Pro-Val-Lys-Lys-Pro-Val | 58 |
| | SEQ ID NO:16 |

BRIEF DESCRIPTION OF THE DRAWINGS

FIG. 1 depicts the organization of the picornavirus genes and their nomenclature.

FIG. 2 depicts the amino acid sequence of FMDV 3A protein (SEQ ID NO:1).

FIG. 3 depicts the amino acid sequence of FMDV 3B protein (SEQ ID NO:2).

FIG. 4 depicts the amino acid sequence of FMDV 3C protein (SEQ ID NO:3).

FIGS. 5A and 5B graphically depict the immunoreactivity of a panel of bovine convalescent sera, bovine vaccinated sera, normal bovine sera, guinea pig convalescent sera, and normal guinea pig sera with FIG. 5B for a mixture of two FMDV 3A and 3B-derived peptides (#2372, SEQ ID NO:16+#2374, SEQ ID NO:14) and FIG. 5A for a FMDV 3B-derived peptide (i.e., #2372, SEQ ID NO:16).

FIGS. 6A, 6B and 6C graphically depict the immunoreactivity of six seroconversion series of swine sera from infected (FIGS. 6A and 6B) or vaccinated (FIG. 6C) animals with FMDV 3B-derived peptide (i.e., #2372).

FIGS. 7A and 7B graphically depict the immunoreactivity of two seroconversion series of bovine sera from infected (FIG. 7A) or vaccinated (FIG. 7B) animals with a mixture of FMDV 3A and 3B-derived peptides (i.e., #2372+#2374).

DETAILED DESCRIPTION OF THE INVENTION

Figure 8A:
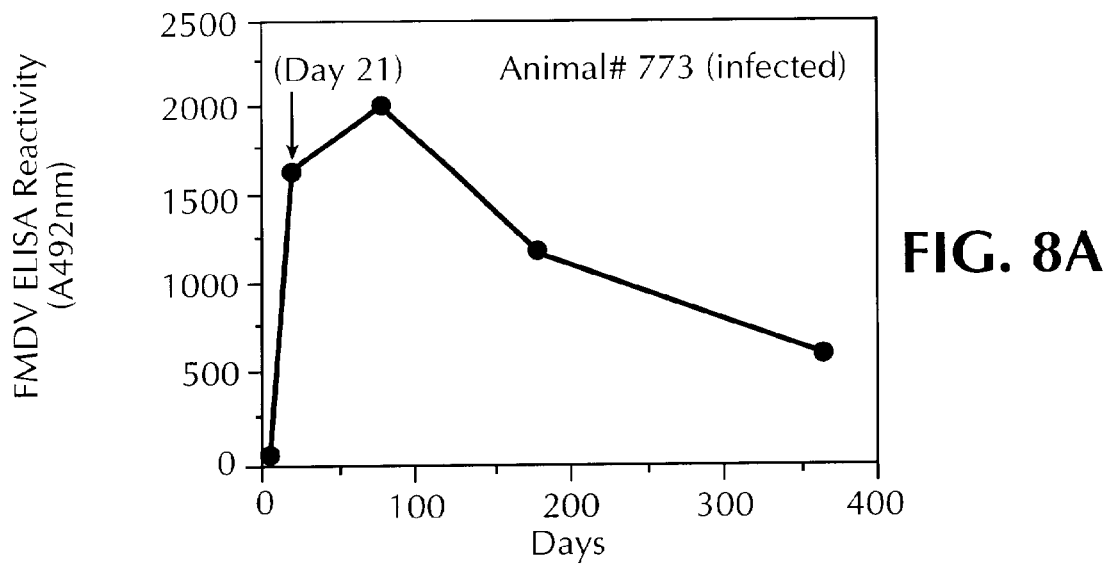
FIGS. 8A and 8B graphically depict the immunoreactivity of two seroconversion series of bovine sera from infected (FIG. 8A) or vaccinated (FIG. 8B) animals with FMDV 3B-derived peptide (i.e., #2372).

In accordance with the present invention, extensive serological analysis has led to the identification of immunoreactive peptides that are useful in the detection of FMDV antibodies, diagnosis of FMDV infection, and differentiation of infected from vaccinated animals. The peptides of this invention comprise epitopes selected from the group consisting of SEQ ID NOS: 4–13 as listed in Table 1. The epitopes represent sites which are immunoreactive to antibodies to FMDV non-structural proteins 3A, 3B or 3C. The preferred epitopes are represented by SEQ ID NO:7–10. The epitopes represented by SEQ ID NOS: 4–13 may be employed as peptides or as a part of longer peptides as in SEQ ID NOS: 14–16 of Table 2. For convenience, SEQ ID NOS: 4–13 together with SEQ ID NOS: 14–16 are sometimes referred to herein collectively as the subject peptides, or the peptides. The peptides may also be in branched form as set forth below.

The subject peptides can include from 1 to about 5 additional amino acids, including unnatural amino acids, at the terminal amino acids. For example, the sequence KKK (Lys-Lys-Lys) can be added to the amino terminus of any of these peptides. For branched peptides, an M (methionine) residue can be placed at the carboxyl terminus of the peptide moiety, i.e. between the peptide moiety and the branch structure.

The subject peptides also include analogs thereof, meaning homologs from a strain or an isolate of FMDV corresponding to SEQ ID NOS: 4–16 and peptides having conservative substitutions such that the secondary conformation thereof remain unchanged. Examples of such conservative substitutions include amino acid residues having substantially the same hydrophobicity, size, and charge as the original amino acid residue. Such substitutions are generally well known to those skilled in the art of peptide chemistry. For example, conservative substitutions include proline for glycine and vice versa; alanine or valine for glycine and vice versa; isoleucine for leucine and vice versa; histidine for lysine and vice versa; serine for asparagine and vice versa; threonine for cysteine and vice versa; serine or alanine for threonine and vice versa; glutamine for asparagine and vice versa; tryptophan for tyrosine and vice versa; and arginine for glutamate and vice versa.

The subject peptides can also be used to form conjugates, i.e., the peptides can be coupled directly or indirectly, by methods known in the art, to carrier proteins such as bovine serum albumin (BSA), human serum albumin (HSA), or to red blood cells or latex particles.

As used herein, natural amino acids are the 20 amino acids commonly found in proteins (i.e. alanine, aspartic acid, asparagine, arginine, cysteine, glycine, glutamine, glutamic acid, histidine, isoleucine, leucine, lysine, methionine, phenylalanine, proline, serine, threonine, tyrosine, tryptophan and valine). As used herein the natural amino acids include both the D- and L- forms of such amino acids.

As used herein "unnatural amino acids" include both D- and L- forms of any other amino acids whether found in a protein, whether found in nature or whether synthetically produced. Unnatural amino acids can include, but are not limited to, β-alanine, ornithine, norleucine, norvaline, hydroxyproline, thyroxine, gamma-amino butyric acid, homoserine, citrulline and the like.

The linear peptides of this invention are represented by the formula

[peptide]-Y wherein Y is —OH or —NH$_2$, and include mixtures, conjugates and polymers of these linear peptides. The peptides comprise at least one antigenic site which is specifically immunoreactive with antibodies against FMDV.

The branched peptides of the present invention are represented by one of the formulae:

[peptide]$_2$X

[peptide]$_4$X$_2$X

[peptide]$_8$X$_4$X$_2$X

[peptide]$_{16}$X$_8$X$_4$X$_2$X wherein X is an amino acid or an amino acid analogue having two amino groups and one carboxyl group, each group capable of forming a peptide bond linkage. Preferably X is lysine or a lysine analog such as ornithine. The amino acid analogue can be an α-amino acid, a β-amino acid, or any other either natural or non-natural amino acid with two amino groups and one carboxyl group available for forming peptide bonds. Preferred branched peptides of the invention are dimers, tetramers, octamers and hexadecamers, especially those having a branching core structure composed of lysine, i.e. where X is lysine.

The peptide moiety of the linear or branched peptides can vary in length from about 15 to about 75 amino acid residues. Preferably the peptide moieties contain about 17 to about 70 amino acid residues.

The present invention also includes compositions containing the subject peptides. Preferably such compositions contain from one to 10 peptides, and, more preferably from one to four peptides and even more preferably from one to two peptides.

In a preferred embodiment, the peptide compositions of the present invention include peptides with SEQ ID NOS:4–16, and preferably peptides with SEQ ID NOS:14–16. The peptide compositions of the present invention also include mixtures of the peptides. The effective ratio of the peptides in such mixtures can be readily determined by one of ordinary skill in the art. Typically, these ratios range from about 1 to about 50 on a weight basis of each peptide in the mixture.

The peptide compositions, peptides and mixtures described herein are useful for the detection of antibodies to FMDV in animal body fluids, the diagnosis of FMDV infection and differentiation of infected from vaccinated animals.

To determine the efficacy of the subject peptides in detecting FMDV antibodies, the peptides are tested for their immunoreactivity with serum/plasma specimens obtained from FMDV infected, vaccinated or naive animals from various species (e.g., cattle, swine and guinea pigs). Such FMDV-specific serum panels are provided in part by Plum Island Animal Disease Center, U.S. Department of Agriculture (PIADC USDA) and in part through commercially available sources. It is important to obtain sera from representative populations because the definition of the antigenic sites for identifying antigenic peptides is dependent on the panel of sera used. The more closely the panel represents the population with seropositivity for antibodies for an antigenic site, the greater the chance that the antigenic site will be identified and thoroughly mapped.

The peptides can be readily synthesized using standard techniques, such as the Merrifield method of synthesis (Merrifield, *J Am Chem Soc,* 1963, 85:2149–2154) and the myriad of available improvements on that technology, see e.g., *Synthetic Peptides: A User's Guide,* Grant, ed. (1992) W.H. Freeman & Co., New York, pp. 382; Jones (1994) *The Chemical Synthesis of Peptides,* Clarendon Press, Oxford, pp. 230.

Another problem which can be minimized by using peptides rather than recombinantly expressed proteins is the rate of false-positive results caused by the presence of antigenic material co-purified with FMDV recombinant proteins. For example, certain normal animals have antibodies to Escherichia coli, yeast or baculovirus proteins which are crossreactive with the antigenic materials from the expression systems used in recombinant protein-based diagnostic tests. Sera from such normal animals can show a false positive reaction in such immunoassay which false reaction is eliminated in immunoassay of the present invention.

Moreover, because the peptide compositions of the present invention are synthetically prepared, the quality can be controlled and as a result, reproducibility of the test results can be assured. The cost for immunoassay employing peptides is relatively low. This is because very small amounts of peptides are required for each test procedure, and the expense of preparing peptides is relatively low compared to recombinantly produced proteins.

The peptides and peptide compositions prepared in accordance with the present invention are useful as reagents in immunoassay to detect antibodies to FMDV as a result of infection and differentiate the FMDV infected animals from the vaccinated animals. The immunoassay procedures suitable include enzyme-linked immunoadsorbent assay (ELISA), enzyme immunodot assay, agglutination assay, antibody-peptide-antibody sandwich assay, peptide-antibody-peptide sandwich assay, or other well-known immunoassay formats to the ordinarily skilled artisan. These immunoassay formats and procedures have been described in many standard immunology manuals and texts, see for example, by Harlow et al., (1988) *Antibodies: A Laboratory Manual,* Cold Spring Harbor Laboratory Press, Cold Spring Harbor, N.Y., 726 pp. The preferred immunoassay formats are ELISA and agglutination, the most preferred being ELISA. In the ELISA format, preferably a solid phase is coated with the above-identified peptide compositions of the present invention. Other ELISA formats and procedures are well known in the art.

The immunoassays of the present invention are used to screen body fluids and tissues for the presence of FMDV-reactive antibody and thereby aid in the diagnosis of FMDV infection and differentiate infected from vaccinated animals. The body fluids which can be screened include blood and blood fractions (e.g., plasma and serum), saliva, or any other fluid which is suspected of containing antibodies against FMDV.

Another aspect of the present invention is directed to a kit for the detection of FMDV antibodies or diagnosis of FMDV infection in mammalian body fluids (e.g., serum, tissue extracts, tissue fluids). The kit can be compartmentalized to receive a first container adapted to contain one or more of the peptides (i.e., a peptide composition) of this invention.

Preferably the kit of this invention is an ELISA or an agglutination test kit for detecting of FMDV antibodies and thereby diagnosis of FMDV infection. For an ELISA test kit, the kit contains (a) a container (e.g., a 96-well plate) having a solid phase coated with one of the subject peptide compositions; (b) a negative control sample; (c) a positive control sample; (d) specimen diluent and (e) antibodies to species-specific (e.g., bovine, swine or horse) IgG, or recombinant protein A, protein G or protein A/G known to be reactive with all types or subtypes of immunoglobulins from multiple species, which protein is labelled with a reporter molecule. If the reporter molecule is an enzyme, then the kit also contains a substrate for said enzyme.

To use the kit of the present invention, a sample of body fluid to be tested, diluted in sample diluent if necessary, is placed in contact with the peptide coated solid phase for a time and under conditions for any antibodies present in the body fluid to bind to the peptide. After removal of unbound material (e.g., by washing with phosphate buffered saline), the secondary complex is contacted with labelled antibodies to species-specific IgG or labelled protein A, protein G, or protein A/G. These antibodies or proteins A, G or A/G bind to the secondary complex to form a tertiary complex and, since the second antibodies or proteins A, or G or A/G are labeled with a reporter molecule, when subjected to a detecting means, the tertiary complex is detected. The reporter molecule can be an enzyme, radioisotope, fluorophore, bioluminescent molecule, chemiluminescent molecule, biotin, avidin, streptavidin or the like. For ELISA the reporter molecule is preferably an enzyme.

The examples serve to illustrate the present invention and are not to be used to limit the scope of the invention.

EXAMPLE 1

A Typical ELISA Assay Method

The wells of 96-well plates are coated separately for 1 hour at 37° with 2 μg/mL of FMDV nonstructural protein-derived peptide or mixtures thereof using 100 μL per well in 10 mM NaHCO$_3$ buffer, pH 9.5 unless noted otherwise.

The peptide-coated wells are incubated with 250 μL of 3% by weight of gelatin in PBS in 37° C. for 1 hour to block non-specific protein binding sites, followed by three washes with PBS containing 0.05% by volume of TWEEN 20 and dried. Animal sera positive for FMDV-reactive antibody are diluted 1:20 or 1:100 volume to volume with PBS containing 20% by volume normal goat serum, 1% by weight gelatin and 0.05% by volume TWEEN 20 as described in the examples below. 100 μL of the diluted specimens are added to each of the wells and allowed to react for 60 minutes at 37° C.

The wells are then washed six times with 0.05% by volume TWEEN 20 in PBS in order to remove unbound antibodies. Horseradish peroxidase-conjugated goat anti-bovine, swine or guinea pig IgG is used as a second tracer to bind with the FMDV antibody-peptide antigen complex formed in positive wells. 100 μL of peroxidase-labeled goat anti-species specific IgG at a pre-titered optimal dilution, in 1% by volume normal goat serum, 0.05% by volume TWEEN 20 in PBS is added to each well and incubated at 37° C. for another 30 minutes.

The wells are washed six times with 0.05% by volume TWEEN 20 in PBS to remove unbound antibody and reacted with 100 μL of the substrate mixture containing 0.04% by weight orthophenylenediamine (OPD) and 0.12% by volume hydrogen peroxide in sodium citrate buffer, pH 5.0 for another 15 minutes. This substrate mixture is used to detect the peroxidase label by forming a colored product. Reactions are stopped by the addition of 100 μL of 1.0M H$_2$SO$_4$ and absorbance at 492 nm (A$_{492}$) determined.

EXAMPLE 2

Immunoreactivity of FMDV Nonstructural Protein-Derived Peptides

In practice, theoretical prediction of antigenic features by algorithm has proven less useful than empirical analysis and experiment. To empirically identify epitopes, specific features of the predicted secondary structure in proteins known to be antigenic are used to select the possible peptides. These are then synthesized and tested for antigenicity.

Based on the above concept, a large collection of overlapping peptides of lengths varying from 15 to 60 residues with amino acid sequences derived from FMDV 3A, 3B and 3C. proteins (Table 1) were designed and tested against a panel of positive sera (FIGS. 2, 3 and 4).

Initially, the immunoreactivity of 34 FMDV nonstructural protein-derived peptides (Table 3), each with its corresponding amino acid sequence shown in Table 1 and FIGS. 2–4, was determined using FMDV-infected serum samples from nine guinea pigs and 2 bovines (panel 1) at a 1:20 dilution, in an ELISA assay format described in Example 1. Groups of 2 or 3 peptides, wherein each peptide was coated on the microtiter wells at coating concentration of 2 μg/mL and tested. Those providing A$_{492}$ values higher than 0.9 were noted to aid the recognition of a immunoreactivity pattern between the FMDV nonstructural protein-derived peptides and the FMDV-infected sera. The results indicate that peptides #2311–#2315 react more strongly with most of the sera containing FMDV antibody than peptides #2319–#2321, #2322–#2324 and #2328–#2332.

TABLE 3

A492 nm; ELISA (FMDV Peptide coated microtiter wells)

|  | FMDV-3A | | | | FMDV-3B | | FMDV-3C | | | | | |
| --- | --- | --- | --- | --- | --- | --- | --- | --- | --- | --- | --- | --- |
| Serum Panel 1 I.D. Number | 2299–2301 | 2302–2304 | 2305–2307 | 2308–2310 | 2311–2313 | 2314, 2315 | 2316–2318 | 2319–2321 | 2322–2324 | 2325–2327 | 2328–2330 | 2331, 2332 |
| GP-R00023 | 0.323 | 0.939* | 0.284 | 0.287 | 0.560 | 1.566* | 0.296 | 0.355 | 0.591 | 0.403 | 0.318 | 0.356 |
| GP-R00059 | 0.622 | 0.644 | 0.236 | 0.256 | 1.770* | 1.817* | 0.277 | 0.314 | 0.667 | 0.321 | 0.258 | 0.299 |
| GP-R00071 | 0.958 | 0.609 | 0.379 | 0.438 | 1.635* | 1.828* | 0.399 | 0.461 | 0.837 | 0.478 | 0.431 | 0.494 |
| GP-R00079 | 0.516 | 0.478 | 0.458 | 0.441 | 1.707* | 1.794* | 0.446 | 0.546 | 0.897 | 0.580 | 0.048 | 0.537 |
| GP-R00100 | 0.404 | 0.414 | 0.375 | 0.432 | 0.865 | 1.679* | 0.369 | 0.484 | 0.632 | 0.468 | 0.389 | 0.473 |
| GP-R00101 | 0.574 | 0.727 | 0.409 | 0.417 | 0.931* | 1.647* | 0.392 | 0.461 | 0.836 | 0.522 | 0.433 | 0.457 |
| GP-R00105 | 0.534 | 0.433 | 0.459 | 0.485 | 1.635* | 1.504* | 0.443 | 0.539 | 0.767 | 0.461 | 0.471 | 0.565 |
| GP-R00116 | 0.756 | 0.563 | 0.690 | 0.787 | 0.672 | 1.770* | 0.706 | 0.908* | 1.026* | 0.872 | 1.043* | 0.931* |
| GP-R00124 | 0.711 | 0.674 | 0.853 | 0.804 | 1.144* | 1.796* | 0.784 | 0.939* | 1.198* | 0.963* | 0.822 | 0.911* |
| Normal GP serum | 0.095 | 0.091 | 0.100 | 0.104 | 0.094 | 0.096 | 0.102 | 0.117 | 0.148 | 0.130 | 0.105 | 0.121 |
| BOV-R00690 | 0.329 | 0.315 | 0.396 | 0.398 | 0.370 | 0.579 | 0.372 | 0.435 | 0.512 | 0.559 | 0.427 | 0.458 |
| BOV-R01053 | 0.146 | 0.198 | 0.165 | 0.217 | 1.659* | 1.687* | 0.165 | 0.167 | 0.287 | 0.216 | 0.157 | 0.982* |
| Normal BOV serum | 0.098 | 0.099 | 0.100 | 0.098 | 0.079 | 0.083 | 0.083 | 0.089 | 0.117 | 0.145 | 0.114 | 0.118 |
| Specimen Diluent | 0.059 | 0.049 | 0.053 | 0.048 | 0.051 | 0.048 | 0.049 | 0.050 | 0.052 | 0.051 | 0.047 | 0.054 |

EXAMPLE 3

Immunodominant Peptides Derived from the FMDV 3A, 3B AND 3C Proteins

The immunoreactivity of the FMDV peptides identified in Example 2 were further evaluated by testing individual peptide-coated wells (2 μg/mL) and with the 3 FMDV positive and 2 normal control sera of Panel 2. In order to more precisely rank the peptides by relative immunoreactivities, the specimens were tested at a 1:100 dilution rather than the 1:20 dilution previously employed in Example 2.

Results shown in Table 4 indicate that peptides #2300 (SEQ ID NO:4), #2301 (SEQ ID NO:5), #2304 (SEQ ID NO:6), #2312 (SEQ ID NO: 7), #2313 (SEQ ID NO:8), #2314 (SEQ ID NO:9), #2315 (SEQ ID NO:10), #2322 (SEQ ID NO:11), #2324 (SEQ ID NO:12), and #2332 (SEQ ID NO:13) exhibited stronger FMDV immunoreactivity, as shown by asterisks, than the rest of the peptides.

Several of the FMDV 3C-derived peptides exhibited strong reactivity with sera GPR00116, GPR00124 and BOVR001053 as shown in Table 3. However, they were found to be nonreactive or moderately reactive with sera GPR00023, GPR00079, and BOVR01053. This indicates that the epitopes which reside in these proteins are conformational.

TABLE 4

A 492 nm; ELISA (FMDB Peptide Coated microtiter wells) Serum Panel 2

| | Peptide Code | R00023 (GP) | R00079 (GP) | NORMAL GP Serum | R01053 (BOV) | Normal Bovine Serum | Sample Diluent |
| --- | --- | --- | --- | --- | --- | --- | --- |
| FMDV-3A | 2299 | 0.144 | 0.198 | 0.066 | 0.102 | 0.102 | 0.049 |
| | 2300 | 0.148 | 0.409* | 0.067 | 0.102 | 0.101 | 0.051 |
| | 2301 | 0.297* | 0.231 | 0.067 | 0.103 | 0.102 | 0.052 |
| | 2302 | 0.138 | 0.187 | 0.068 | 0.102 | 0.127 | 0.053 |
| | 2303 | 0.129 | 0.189 | 0.067 | 0.100 | 0.098 | 0.058 |
| | 2304 | 0.450* | 0.199 | 0.065 | 0.111 | 0.104 | 0.051 |
| | 2305 | 0.153 | 0.191 | 0.064 | 0.111 | 0.103 | 0.050 |
| | 2306 | 0.190 | 0.229 | 0.072 | 0.102 | 0.101 | 0.055 |
| | 2307 | 0.139 | 0.190 | 0.070 | 0.099 | 0.093 | 0.054 |
| | 2308 | 0.183 | 0.224 | 0.070 | 0.108 | 0.104 | 0.054 |
| | 2309 | 0.154 | 0.218 | 0.060 | 0.111 | 0.120 | 0.058 |
| | 2310 | 0.149 | 0.223 | 0.067 | 0.119 | 0.115 | 0.055 |
| FMDV-3B | 2311 | 0.147 | 0.200 | 0.065 | 0.102 | 0.105 | 0.054 |
| | 2312 | 0.275 | 0.649 | 0.066 | 0.509* | 0.125 | 0.052 |
| | 2313 | 0.161 | 1.601* | 0.066 | 0.142 | 0.138 | 0.054 |
| | 2314 | 1.606* | 1.798* | 0.071 | 0.864* | 0.205 | 0.060 |

TABLE 4-continued

A 492 nm; ELISA (FMDB Peptide Coated microtiter wells)
Serum Panel 2

| Peptide Code | | R00023 (GP) | R00079 (GP) | NORMAL GP Serum | R01053 (BOV) | Normal Bovine Serum | Sample Diluent |
|---|---|---|---|---|---|---|---|
| | 2315 | 1.106* | 1.738* | 0.068 | 0.286 | 0.109 | 0.053 |
| FMDV-3C | 2316 | 0.263 | 0.211 | 0.069 | 0.099 | 0.085 | 0.053 |
| | 2317 | 0.167 | 0.232 | 0.076 | 0.110 | 0.119 | 0.055 |
| | 2318 | 0.148 | 0.200 | 0.071 | 0.113 | 0.123 | 0.058 |
| | 2319 | 0.186 | 0.248 | 0.078 | 0.124 | 0.119 | 0.060 |
| | 2320 | 0.155 | 0.225 | 0.074 | 0.124 | 0.127 | 0.068 |
| | 2321 | 0.199 | 0.237 | 0.075 | 0.120 | 0.118 | 0.057 |
| | 2322 | 0.242 | 0.398* | 0.080 | 0.164 | 0.121 | 0.055 |
| | 2323 | 0.148 | 0.216 | 0.072 | 0.101 | 0.114 | 0.054 |
| | 2324 | 0.233 | 0.355* | 0.089 | 0.136 | 0.104 | 0.054 |
| | 2325 | 0.149 | 0.206 | 0.071 | 0.110 | 0.097 | 0.061 |
| | 2326 | 0.156 | 0.219 | 0.071 | 0.117 | 0.124 | 0.053 |
| | 2327 | 0.173 | 0.260 | 0.084 | 0.113 | 0.110 | 0.055 |
| | 2328 | 0.173 | 0.204 | 0.081 | 0.109 | 0.098 | 0.050 |
| | 2329 | 0.196 | 0.234 | 0.085 | 0.131 | 0.106 | 0.057 |
| | 2330 | 0.178 | 0.226 | 0.177 | 0.120 | 0.105 | 0.056 |
| | 2331 | 0.185 | 0.246 | 0.078 | 0.121 | 0.095 | 0.055 |
| | 2332 | 0.179 | 0.271 | 0.082 | 0.323* | 0.114 | 0.061 |

EXAMPLE 4

Comparisons for Relative Immunoreactivities of Short and Long FMDV 3A and 3B-Derived Peptides Ten FMDV 3A and 3B-derived peptides of varying lengths were further compared for their relative immunoreactivities with Panel 2 at a 1:20 dilution as shown in Table 5. The three peptides designated #2372, based on FMDV 3B protein, #2373 and #2374, based on FMDV 3A protein, were synthesized to have amino acid sequences as follows: The amino acid sequence of peptide #2374 corresponds to that of SEQ ID NO:14 with two lysine residues added at the N-terminus. The amino acid sequence of #2373 corresponds to that of SEQ ID NO:15 with three lysines residues added at the N-terminus. The amino acid sequence of #2372 corresponds to that of SEQ ID NO:16 with three lysine residues added at the N-terminus.

The results indicate that peptides #2374, #2314, #2315 and #2372 (with asterisks) exhibited the highest FMDV-immunoreactivity and were thus most desirable for use in the construction of an immunoassay for the detection of FMDV antibodies. In contrast, normal guinea pig serum, normal bovine serum or specimen diluent gave clean background readings as were the wells coated with unrelated antigens, e.g., peptide 804 and protein BSA.

EXAMPLE 5

Evaluation of FMDV-Enzyme Immunoassay in Infected, Vaccinated and Naive Animal Populations Characterization of FMDV-reactive bovine and swine sera. The immunoreactivities of a large number of bovine and swine sera from animals kindly provided by PIADC, USDA were characterized. A collection of the sera were certified as convalescent by VIAA and a collection were from certified vaccinated animals, some of which had a history of multiple vaccinations. A large number of negative sera from naive animals from the same herd and also from a broad geographic range were also used to evaluate the specificity of the assays.

The peptide compositions used in this experiment were peptides #2372 and #2374 as described in Example 4.

Determination of anti-FMDV reactivity by FMDV ELISA peptides. Anti-FMDV peptide ELISAs were conducted by coating 96-well microtiter plates by 1 hr incubation at 37° C. with (a) a mixture of peptides #2374 (FMDV 3A) and #2372 (FMDV 3B) at 2 μg/mL and 0.5 μg/mL respectively; (b) peptide #2372 (FMDV 3B) alone at 0.5 μg/mL, or (c) peptide #2374 (FMDV 3A) alone at 2 μg/mL using 100 μL per well in 10 mM NaHCO₃ buffer, pH 9.5. The FMDV peptide-coated wells were incubated with 250 μL of 3% by weight of gelatin in PBS at 37° C. for 1 hr to block

TABLE 5

A 492 nm; ELISA (FMDV peptide coated microtiter wells)

| Serum Panel 2 | FMDV-3A | | | | | FMDV-3B | | | | | Unrelated Ags | |
|---|---|---|---|---|---|---|---|---|---|---|---|---|
| I.D. No. | 2300 | 2301 | 2304 | 2373 | 2374 | 2312 | 2313 | 2314 | 2315 | 2372 | 804 | BSA |
| GP-R00023 | 0.289 | 0.250 | 1.062* | 2.131* | 2.254* | 0.702 | 0.339 | >3.0* | 2.130* | 2.255 | 0.149 | 0.143 |
| GP-R00079 | 0.300 | 0.325 | 0.360 | 1.453* | >3.0* | 1.580* | >3.0* | >3.0* | >3.0* | 2.695* | 0.206 | 0.243 |
| Normal GP serum | 0.060 | 0.064 | 0.067 | 0.061 | 0.060 | 0.064 | 0.064 | 0.059 | 0.057 | 0.067 | 0.063 | 0.063 |
| BOV-R01053 | 0.081 | 0.084 | 0.113 | 0.291 | 0.544* | 0.251 | 0.180 | 0.700* | 0.302 | 1.271* | 0.082 | 0.084 |
| Normal BOV serum | 0.114 | 0.121 | 0.129 | 0.122 | 0.123 | 0.105 | 0.111 | 0.110 | 0.114 | 0.176 | 0.118 | 0.121 |
| Specimen Diluent | 0.088 | 0.079 | 0.079 | 0.075 | 0.079 | 0.079 | 0.074 | 0.077 | 0.077 | 0.077 | 0.072 | 0.093 | non-specific protein binding sites, washed three times with PBS containing 0.05% by volume TWEEN 20 and then dried. Test samples were diluted with PBS containing 20% by volume normal goat serum, 1% by weight gelatin and 0.05% by volume TWEEN 20 at dilutions of 1:20 volume to volume unless indicated otherwise. 100 μL of the diluted sample was added to each of the wells and allowed to react for 1 hr at 37° C. The wells were then washed six times with 0.05% by volume TWEEN 20 in PBS to remove unbound antibodies. 100 μL of horseradish peroxidase labeled goat anti-bovine IgG guinea pig antibody, or goat anti-swine IgG at their respective predetermined optimal dilutions in 1% by volume normal goat serum, 0.05% by volume TWEEN 20 in PBS were added to each well and incubated at 37° C. for 30 minutes. The wells were washed six times with 0.05% by volume TWEEN 20 in PBS to remove unbound labeled antibody conjugate and reacted with 100 μL of the substrate mixture containing 0.04% by weight orthophenylenediamine (OPD) and 0.12% by volume hydrogen peroxide in sodium citrate buffer pH 5.0, for 15 minutes. Reactions were stopped by the addition of 100 μL of 1.0 M $H_2SO_4$ and the absorbance, $A_{492}$, is measured.

Criteria for interpretation An $A_{492}$ greater than the mean $A_{492}$ plus three standard deviations for normal sera is regarded as significant reactivity in an ELISA format. For a commercially useful antigen, an optical density value equal to about 2.00 $A_{492}$ at a 1:21 dilution of a strongly reactive serum is desired, with background non-reactive control values less than $A_{492}$=0.4.

Results

A collection of cattle and swine sera provided under code by PIADC, USDA were tested in three individual assays using FMDV peptide:
1. #2372 (0.5 μg/mL) (i.e., assay 3B),
2. #2372 (0.5 μg/mL)+#2374 (2 μg/mL) (i.e., assay 3A+3B) or
3. #2374 (2 μg/mL)(i.e., assay 3A) as the coating antigen. These samples were tested at 1:20, 1:50 and 1:100 dilutions to assess their respective reactivities in the three assays.

Upon completion of the testing, the samples were decoded by PIADC, USDA. Detailed descriptions were provided for each of the specimens including the clinical history, type of FMDV infection encountered, type of FMDV vaccine received, and date of sera collection. The date of collection was provided for samples from the seroconversion series following infection or vaccination.

In order to evaluate the sensitivity and specificity of these assays, sera from animals infected or vaccinated with different types and subtypes (e.g., SAT, C, O, A, Asia) of FMDV, from geographic distinct regions (e.g. Iraq, India, Kenya, Turkey, etc) were included. Upon a close review of the decoded results as shown in Table 6, an unexpectedly high accuracy both in sensitivity and specificity was observed for all three immunoassays at all three (1:20, 1:50 and 1:100) serum dilutions. In general, all sera from infected animals (coded as BCS) exhibited high reactivities whereas sera from vaccinated or naive animals (BVS AND NEG) exhibited near background reactivities.

Figures 5A, 5B:
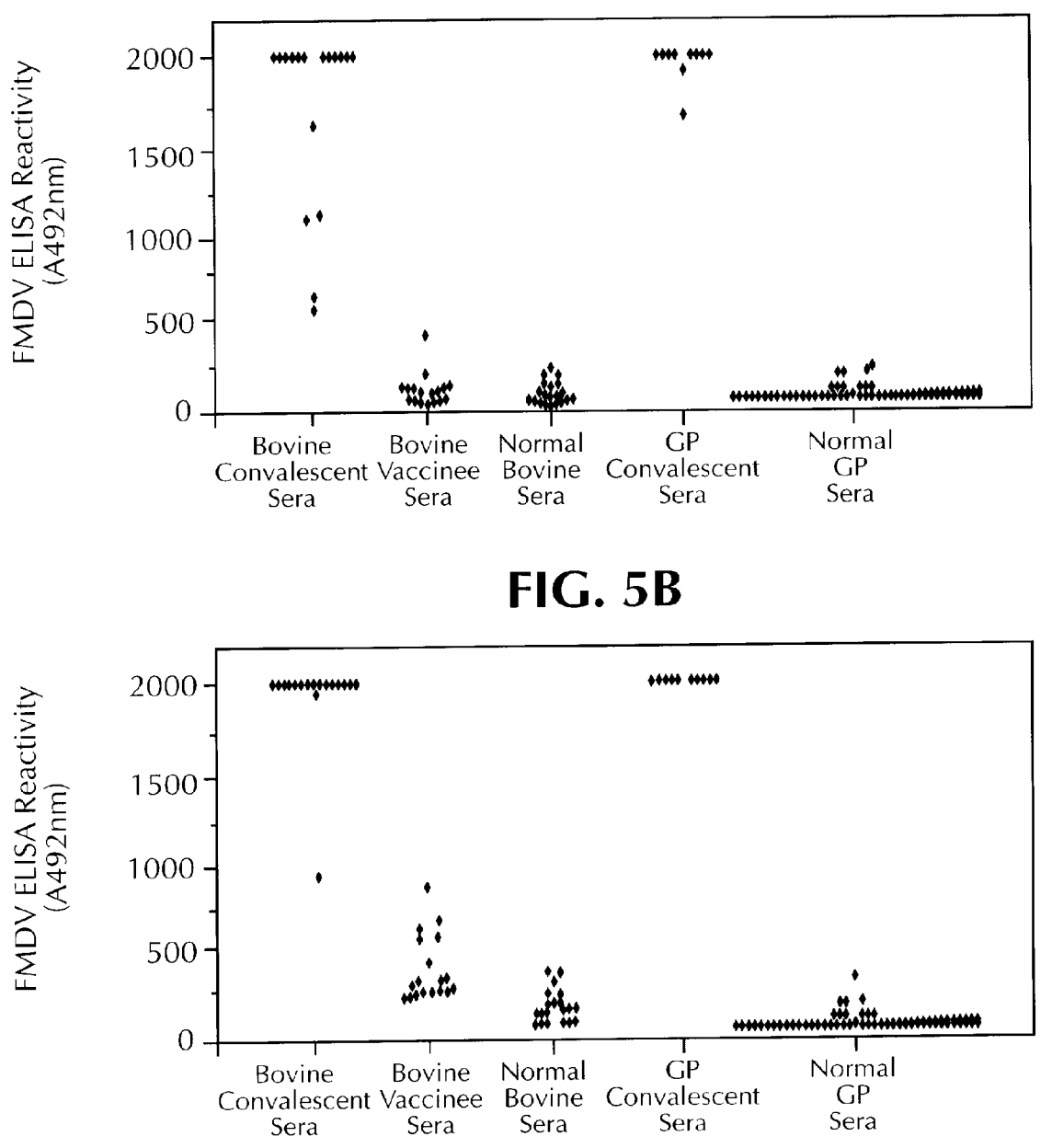

Further analysis of normal bovine and normal guinea pig sera along with additional sera obtained from infected guinea pigs reconfirmed the efficacy of these assays as depicted in FIGS. 5A and B. Except for three sera from vaccinated animals demonstrating a borderline reactivity for assay using peptides from 3B, the assays using the peptides from both 3B and 3A+3B provided results which perfectly differentiated between sera from infected vs. vaccinated or naive animals.

Figures 7A, 7B:
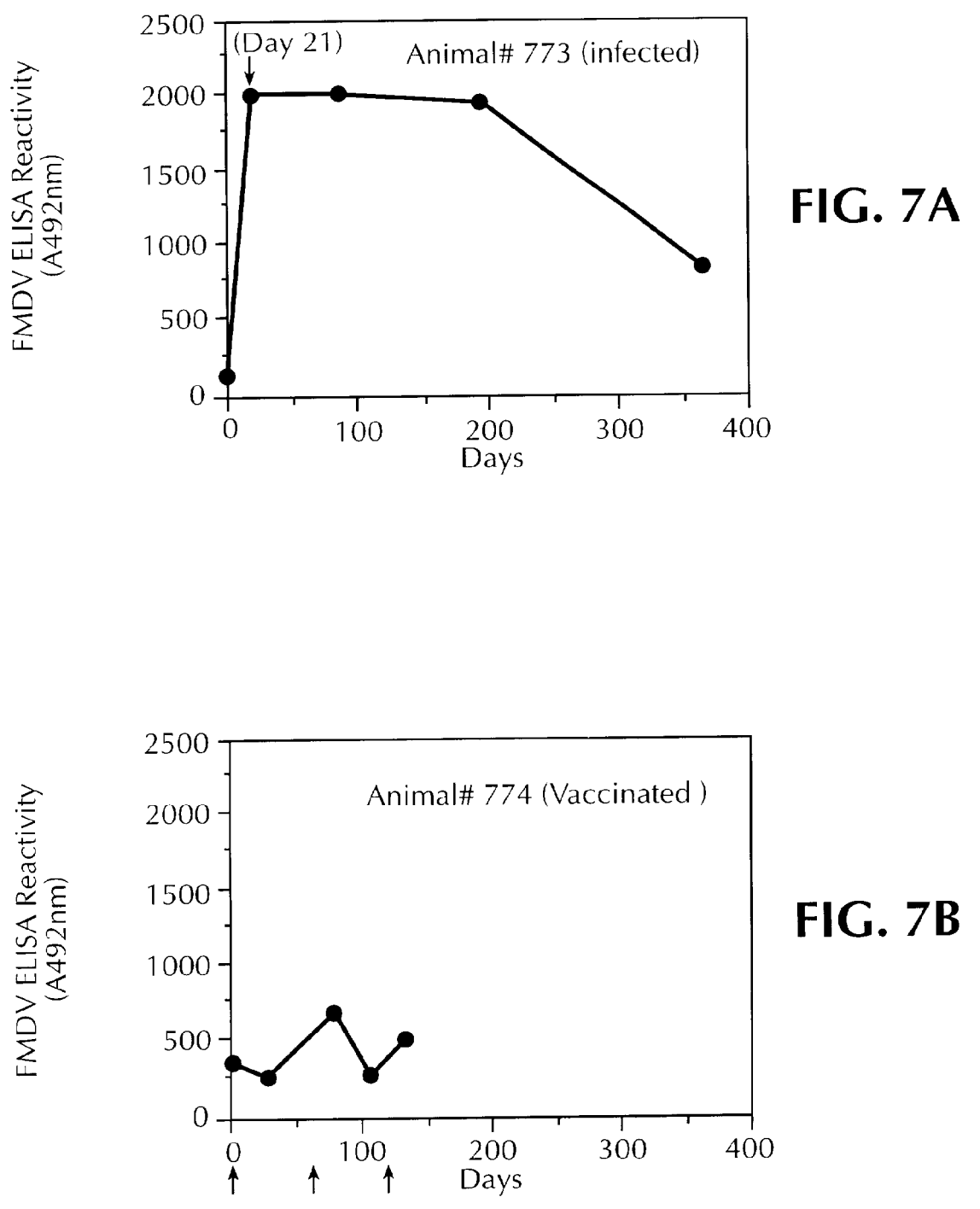
Figure 8B:
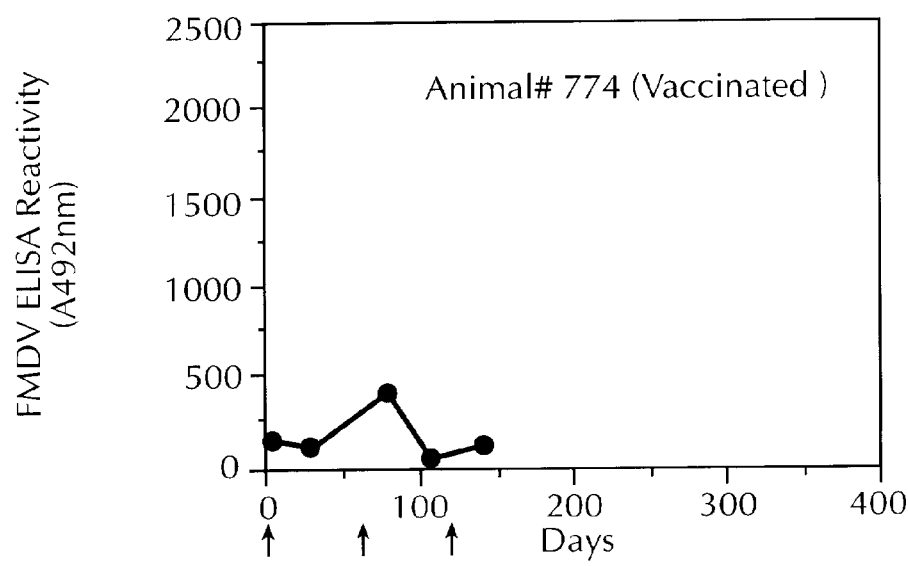

The assay for the sera in the seroconversion series in swine which were infected or vaccinated using the FMDV-3B peptide-based assay (i.e., peptide #2372) of the present invention also provided excellent results. The data indicated that as early as day 11 of infection (FIG. 6) the animals developed strong FMDV 3B reactive antibodies, and such antibodies persisted in high titers throughout at least a 300 day period (FIGS. 6A and B). In contrast, sera from two animals immunized three times (on 0, 65 and 120 days) with a FMDV viral vaccine demonstrated negative reactivity with the FMDV 3B peptide-based immunoassay throughout the 120 day period monitored. Similar results were observed in infected and vaccinated cattle using the 3A/3B peptide mixture and 3B peptide as shown in FIG. 7 and FIG. 8. In summary, a clear distinction in FMDV 3A/3B or FMDV 3B peptide reactivity was observed for sera obtained from infected vs. vaccinated animals. This demonstrates the high efficacy of the FMDV peptide ELISAs.

TABLE 6

| | | | A492 nm; ELISA (FMDV 3A/3B derived peptide coated microwells) | | | | | | | | |
|---|---|---|---|---|---|---|---|---|---|---|---|
| Sample | | | Peptide 2372 Specimen Dilution | | | Peptide 2372 + 2374 Specimen Dilution | | | Peptide 2374 Specimen Dilution | | |
| ID | Code | Description | 1:20 | 1:50 | 1:100 | 1:20 | 1:50 | 1:100 | 1:20 | 1:50 | 1:100 |
| 1 | BCS | SAT 3 BCS 224 BEC 1/65 | 1172 | 521 | 262 | 2000 | 1306 | 681 | 1984 | 996 | 509 |
| 2 | NEG | 95154 4763 | 75 | 38 | 21 | 145 | 69 | 34 | 135 | 51 | 24 |
| 3 | BCS | C Noville BCS 546 | 2000 | 1308 | 719 | 2000 | 2000 | 2000 | 2000 | 2000 | 2028 |
| 4 | BVS | SAT 3 BVS 1508 BEC 1/65 | 101 | 44 | 22 | 242 | 96 | 54 | 234 | 76 | 32 |
| 5 | NEG | 95154 4764 | 33 | 18 | 13 | 151 | 72 | 43 | 163 | 43 | 25 |
| 6 | BVS | O BFS 1860 BVS 1393 | 49 | 28 | 18 | 217 | 96 | 53 | 236 | 84 | 37 |
| 7 | BVS | A IRAQ 24/64 BVS 1401 | 51 | 30 | 23 | 242 | 109 | 28 | 262 | 103 | 43 |
| 8 | BVS | SAT 2 BVS 1527 K183/24 | 118 | 53 | 24 | 401 | 166 | 90 | 398 | 159 | 67 |
| 9 | BCS | C Pando BCS 1409 | 2000 | 1748 | 1118 | 2000 | 2000 | 2000 | 2000 | 2000 | 2000 |
| 10 | NEG | 95154 4777 | 82 | 32 | 25 | 185 | 80 | 46 | 126 | 47 | 23 |
| 11 | BCS | A Kenya 18/66 BCS | 2000 | 2032 | 1535 | 2000 | 2000 | 2000 | 2000 | 2000 | 1852 |
| 12 | NEG | 95154 4762 | 31 | 13 | 12 | 69 | 25 | 22 | 54 | 11 | −3 |
| 13 | BCS | O India 53/79 BCS 518 | 2000 | 1867 | 1164 | 2000 | 2000 | 2000 | 2000 | 2000 | 2000 |
| 14 | BCS | SAT 2 BCS 1199 K1831/74 | 2000 | 2000 | 1649 | 2000 | 2000 | 2000 | 2000 | 2000 | 2000 |
| 15 | BVS | C Pando BVS 1331 | 196 | 100 | 51 | 610 | 243 | 117 | 575 | 199 | 83 |
| 16 | NEG | 95154 4769 | 70 | 40 | 21 | 279 | 81 | 54 | 143 | 60 | 27 |
| 17 | NEG | 95154 4776 | 161 | 71 | 35 | 226 | 110 | 62 | 249 | 118 | 60 |

TABLE 6-continued

| | | | A492 nm; ELISA (FMDV 3A/3B derived peptide coated microwells) | | | | | | | | |
|---|---|---|---|---|---|---|---|---|---|---|---|
| | | | Peptide 2372 Specimen Dilution | | | Peptide 2372 + 2374 Specimen Dilution | | | Peptide 2374 Specimen Dilution | | |
| Sample ID | Code | Description | 1:20 | 1:50 | 1:100 | 1:20 | 1:50 | 1:100 | 1:20 | 1:50 | 1:100 |
| 18 | BCS | A24 Cruz. BCS 430 | 2000 | 2000 | 1832 | 2000 | 2000 | 2000 | 2000 | 2000 | 2000 |
| 19 | NEG | 95154 4761 | 53 | 22 | 14 | 102 | 56 | 32 | 79 | 32 | 8 |
| 20 | NEG | 95154 4771 | 31 | 15 | 7 | 70 | 32 | 16 | 47 | 19 | 7 |
| 21 | BVS | A24 Cruz. BVS 1356 | 58 | 29 | 16 | 558 | 234 | 114 | 495 | 203 | 78 |
| 22 | NEG | 95154 4779 | 39 | 24 | 11 | 114 | 58 | 31 | 95 | 37 | 13 |
| 23 | NEG | 95154 4770 | 112 | 57 | 34 | 132 | 63 | 37 | 113 | 46 | 21 |
| 24 | BVS | O India 53/79 BVS 1382 | 71 | 36 | 15 | 298 | 139 | 63 | 253 | 89 | 43 |
| 25 | BVS | O Turkey 1/78 BVS 1458 | 48 | 23 | 8 | 212 | 98 | 73 | 218 | 87 | 56 |
| 26 | BCS | SAT 1 Bot 1/68 BCS 1200 | 639 | 303 | 119 | 2000 | 1397 | 790 | 1949 | 935 | 593 |
| 27 | BVS | Asia 1 India 8/79 BVS 1400 | 123 | 57 | 30 | 287 | 125 | 78 | 272 | 103 | 58 |
| 28 | NEG | 95154 4778 | 164 | 68 | 31 | 223 | 99 | 61 | 36 | 11 | 10 |
| 29 | BCS | O Turkey 1/78 BCS 1504 | 2038 | 1109 | 557 | 2000 | 2000 | 2000 | 2000 | 2000 | 1797 |
| 30 | NEG | 95154 4766 | 74 | 34 | 18 | 90 | 49 | 59 | 86 | 34 | 13 |
| 31 | NEG | 95154 4773 | 47 | 25 | 17 | 82 | 43 | 34 | 83 | 46 | 35 |
| 32 | BVS | SAT 1 Bot 1/68 BVS 1575 | 113 | 62 | 25 | 291 | 129 | 60 | 294 | 125 | 80 |
| 33 | NEG | 95154 4774 | 89 | 43 | 21 | 93 | 43 | 28 | 92 | 37 | 31 |
| 34 | BCS | 01 Campos BCS 1408 | 2000 | 2017 | 1340 | 2000 | 2000 | 2000 | 2000 | 2000 | 2000 |
| 35 | NEG | 95154 4775 | 123 | 47 | 14 | 152 | 71 | 40 | 168 | 75 | 49 |
| 36 | NEG | 95154 4768 | 52 | 25 | 16 | 175 | 73 | 35 | 178 | 69 | 38 |
| 37 | BVS | 01 Campos BVS 1337 | 132 | 71 | 35 | 233 | 92 | 42 | 179 | 77 | 39 |
| 38 | BVS | A Kenya 18/66 BVS 1422 | 96 | 44 | 25 | 219 | 102 | 57 | 249 | 109 | 57 |
| 39 | NEG | 95154 4772 | 44 | 22 | 18 | 75 | 48 | 27 | 63 | 32 | 20 |
| 40 | BCS | A IRAQ 24/64 BCS 1281 | 2000 | 2000 | 1333 | 2000 | 2000 | 2000 | 2000 | 2000 | 2022 |
| 41 | BVS | C Noville BVS 1268 | 31 | 18 | 13 | 862 | 445 | 170 | 949 | 556 | 200 |
| 42 | NEG | 95154 4780 | 214 | 89 | 44 | 343 | 177 | 72 | 280 | 151 | 62 |
| 43 | BCS | 01 BFS 1860 BCS 565 | 2000 | 2000 | 1764 | 2000 | 2000 | 2000 | 2000 | 2000 | 2000 |
| 44 | NEG | 95154 4767 | 44 | 26 | 19 | 344 | 184 | 82 | 378 | 204 | 98 |
| 45 | BCS | Asia India 8/79 BCS 971 | 2000 | 2000 | 1854 | 2000 | 2000 | 2000 | 2000 | 2000 | 1548 |
| 46 | NEG | 95154 4765 | 126 | 110 | 30 | 182 | 129 | 56 | 206 | 112 | 57 |
| A1 | Bov-SC | Infected at Day 0 | 51 | 27 | 21 | 143 | 80 | 57 | 159 | 81 | 50 |
| A2 | Bov-SC | Infected at day 21 | 1626 | 820 | 472 | 2000 | 1583 | 926 | 1795 | 981 | 490 |
| A3 | Bov-SC | Infected at day 79 | 2000 | 1870 | 1339 | 2000 | 2000 | 2000 | 2000 | 2000 | 1561 |
| A4 | Bov-SC | Infected at day 180 | 1157 | 543 | 291 | 1947 | 1001 | 551 | 1218 | 562 | 235 |
| A5 | Bov-SC | Infected at day 365 | 584 | 251 | 129 | 911 | 406 | 221 | 416 | 182 | 76 |
| A6 | Bov-SC | Vaccinated at Day 0 | 157 | 104 | 60 | 329 | 159 | 88 | 313 | 166 | 77 |
| A7 | Bov-SC | Vaccinated at Day 28 | 115 | 61 | 47 | 252 | 128 | 79 | 262 | 142 | 79 |
| A8 | Bov-SC | Vaccinated at Day 77 (Boosted at Day 63) | 419 | 195 | 119 | 654 | 293 | 150 | 144 | 66 | 33 |
| A9 | Bov-SC | Vaccinated at Day 105 | 68 | 33 | 17 | 260 | 133 | 84 | 252 | 127 | 80 |
| A10 | Bov-SC | Vaccinated at Day 140 (Boosted at Day 119) | 129 | 65 | 35 | 569 | 309 | 162 | 573 | 267 | 153 |
| Pos Control | | | 2000 | 1614 | 911 | 2000 | 2000 | 1451 | 1638 | 731 | 369 |
| Neg Control | | | 47 | 16 | 4 | 134 | 62 | 40 | 92 | 152 | 11 |
| Blank | | | −4 | 3 | 0 | −3 | 1 | 6 | −1 | −2 | 1 |

Keys:
BCS = Bovine Convalescent Sera
BVS = Bovine Vaccinated Sera
NEG = "95154" = Negative Sera
Bov-SC = Bovine Seroconversion Sera

We claim:

1. A peptide having an N-terminus and a C-terminus, useful for the detection of FMDV infection in animals selected from the group consisting of:
   a) one of SEQ ID NOS: 4–16 comprising an immunogenic epitope specific to antibodies of FMDV consisting of 15 to 75 amino acids in a sequence corresponding to a non-structural protein of a strain/isolate of FMDV selected from the group consisting of 3A, 3B and 3C;
   b) a homologue of any one of the peptides of (a) having an amino acid sequence corresponding to a part of a strain/isolate of FMDV;
   c) an analog of any one of the peptides of (a) having an amino acid sequence corresponding to a part of a strain/isolate of FMDV containing a conservative substitution; and
   d) one of (a)–(c) further comprising 1–5 amino acids selected from the group consisting of lysine, methionine, glycine and alanine added to the N-terminus of said peptide, homologue or analog.

2. A peptide according to claim 1 selected from the group consisting of SEQ ID NOS: 14, 15, 16, a homologue of any one of the peptides having an amino acid sequence corresponding to a part of a strain/isolate of FMDV, an analog of any one of the peptides having an amino acid sequence corresponding to a part of a strain/isolate of FMDV containing a conservative substitution any one of said peptides homologoues or analogs with 1–5 amino acids selected from the group consisting of lysine, methionine, glycine and alanine added to the N-terminus.

3. A peptide according to claim 1 wherein the peptide is SEQ ID NO: 16, a homologue thereof having an amino acid sequence corresponding to a part of a strain/isolate of FMDV, an analog thereof having an amino acid sequence corresponding to a part of a strain/isolate of FMDV containing a conservative substitution any one of said peptides, homologues or analogs with 1–5 amino acids selected from the group consisting of lysine, methionine, glycine and alanine added to the N-terminus.

4. An immunoassay method comprising the steps:
   a) Coating a solid phase with a peptide according to claim 1, 2, or 3;
   b) Placing a sample of body fluid, optionally diluted with sample diluent, in contact with the peptide coated solid phase;
   c) Removing any unbound material by washing with phosphate buffered saline;
   d) Contacting the peptide coated solid phase with a reporter molecule labeled antibody;
   e) Optionally providing a substrate for forming a colored product when the reporter molecule is an enzyme.

5. An immunoassay method according to claim 4 wherein the immunoassay is ELISA wherein in step d) the reporter molecule is horseradish-peroxidase.

6. A test kit for an ELISA assay comprising:
   (a) a container having a solid phase coated with a peptide of claim 2 or 3;
   (b) a negative control sample;
   (c) a positive control sample;
   (d) specimen diluent;
   (e) antibodies to species-specific IgG, or protein A, protein G or protein A/G recombinant known to be reactive with all types or subtypes of immunoglobulins from multiple species, which protein is labelled with an enzyme; and
   (f) a substrate for the enzyme.

7. A peptide having an N-terminus and a C-terminus said peptide being useful for the detection of FMDV infection in animals and comprising, an immunogenic epitope specific to antibodies of FMDV, said peptide selected from the group consisting of:
   a) 15 to 75 amino acids in a sequence corresponding to a non-structural protein of a strain/isolate of FMDV selected from the group consisting of 3A, 3B and 3C;
   b) a homologue of the peptide of (a) having an amino acid sequence corresponding to a part of a strain/isolate of FMDV;
   c) an analog of the peptide of (a) having an amino acid sequence corresponding to a part of a strain/isolate of FMDV containing a conservative substitution; and
   d) one of (a)–(c) optionally further comprising 1–5 amino acids selected from the group consisting of lysine, methionine, glycine and alanine added to the N-terminus of said peptide, homologue or analog.

8. A peptide according to claim 7 consisting of 17 to 70 amino acids.

9. A peptide according to claim 7 selected from the group consisting of SEQ ID NOS: 4–13; a homologue of any one of the peptides having an amino acid sequence corresponding to a part of a strain/isolate of FMDV; an analog of any one of the peptide having an amino acid sequence corresponding to a part of a strain/isolate of FMDV containing a conservative substitution; and said peptide, homologue or analog with 1–5 amino acids selected from the group consisting of lysine, methionine, glycine and alanine added to the N-terminus.

10. A peptide according to claim 7 selected from the group consisting of SEQ ID NOS: 7–10; a homologue of any one of the peptides having an amino acid sequence corresponding to a part of a strain/isolate of FMDV; an analog of any one of the peptide having an amino acid sequence corresponding to a part of a strain/isolate of FMDV containing a conservative substitution; and said peptide, homologue of analog with 1–5 amino acids selected from the group consisting of lysine, methionine, glycine and alanine added to the N-terminus.

11. A peptide according to claim 7 wherein the peptide is SEQ ID NO: 14; a homologue thereof corresponding to a part of a strain/isolate of FMDV; an analog thereof having an amino acid sequence corresponding to a part of a strain/isolate of FMDV containing a conservative substitution; and said peptide, homologue or analog with 1–5 amino acids selected from the group consisting of lysine, methionine, glycine and alanine added to the N-terminus.

12. An immunoassay method comprising the steps:
   a) Coating a solid phase with a peptide according to claim 7, 8, 9, 10, or 11;
   b) Placing a sample of body fluid, optionally diluted with sample diluent, in contact with the peptide coated solid phase;
   c) Removing any unbound material by washing with phosphate buffered saline;
   d) Contacting the peptide coated solid phase with a reporter molecule labeled antibody;
   e) Optionally providing a substrate for forming a colored product when the reporter molecule is an enzyme.
   f) detecting said reporter molecule labeled antibody.

13. An immunoassay method according to claim 12 wherein the immunoassay is ELISA wherein in step d) the reporter molecule is horseradish-peroxidase.

14. A test kit for an ELISA assay comprising:
   (a) a container having a solid phase coated with a peptide of claim 7, 8, 9, 10, or 11;

(b) a negative control sample;

(c) a positive control sample;

(d) specimen diluent;

(e) antibodies to species-specific IgG, or protein A, protein G or protein A/G recombinant known to be reactive with all types or subtypes of immunoglobulins from multiple species, which protein is labelled with an enzyme; and (f) a substrate for the enzyme.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
    (A) LENGTH: 153 amino acids
    (B) TYPE: amino acid
    (D) TOPOLOGY: linear (ii) MOLECULE TYPE: peptide (xi) SEQUENCE DESCRIPTION: SEQ ID NO:1:

```
Ile Ser Ile Pro Ser Gln Lys Ser Val Leu Tyr Phe
1               5                   10

Leu Ile Glu Lys Gly Gln His Glu Ala Ala Ile Glu
            15              20

Phe Phe Glu Gly Met Val His Asp Ser Ile Lys Glu
25              30                  35

Glu Leu Arg Pro Leu Ile Gln Gln Thr Ser Phe Val
            40              45

Lys Arg Ala Phe Lys Arg Leu Lys Glu Asn Phe Glu
50              55                  60

Ile Val Ala Leu Cys Leu Thr Leu Leu Ala Asn Ile
            65              70

Val Ile Met Ile Arg Glu Thr Arg Lys Arg Gln Lys
            75              80

Met Val Asp Asp Ala Val Asn Glu Tyr Ile Glu Lys
85              90                  95

Ala Asn Ile Thr Thr Asp Asp Thr Thr Leu Asp Glu
            100             105

Ala Glu Lys Asn Pro Leu Glu Thr Ser Gly Ala Ser
110             115                 120

Thr Val Gly Phe Arg Glu Arg Thr Leu Thr Gly Gln
            125             130

Arg Ala Cys Asn Asp Val Asn Ser Glu Pro Ala Arg
            135             140

Pro Ala Glu Glu Gln Pro Gln Ala Glu
145             150

(2) INFORMATION FOR SEQ ID NO:2:

(i) SEQUENCE CHARACTERISTICS:
        (A) LENGTH: 71 amino acids
        (B) TYPE: amino acid
        (D) TOPOLOGY: linear (ii) MOLECULE TYPE: peptide (xi) SEQUENCE DESCRIPTION: SEQ ID NO:2:

Gly Pro Tyr Thr Gly Pro Leu Glu Arg Gln Arg Pro
1               5                   10

Leu Lys Val Arg Ala Lys Leu Pro Gln Gln Glu Gly
            15              20

Pro Tyr Ala Gly Pro Leu Glu Arg Gln Lys Pro Leu
25              30                  35

Lys Val Lys Ala Lys Ala Pro Val Val Lys Glu Gly
            40              45

Pro Tyr Glu Gly Pro Val Lys Lys Pro Val Ala Leu
            50              55              60

Lys Val Lys Ala Lys Asn Leu Ile Val Thr Glu
            65              70

(2) INFORMATION FOR SEQ ID NO:3:

(i) SEQUENCE CHARACTERISTICS:
        (A) LENGTH: 213 amino acids
        (B) TYPE: amino acid
        (D) TOPOLOGY: linear (ii) MOLECULE TYPE: peptide
```

(xi) SEQUENCE DESCRIPTION: SEQ ID NO:3:

Ser Gly Ala Pro Pro Thr Asp Leu Gln Lys Met Val
1               5                   10

Met Gly Asn Thr Lys Pro Val Glu Leu Ile Leu Asp
            15                  20

Gly Lys Thr Val Ala Ile Cys Cys Ala Thr Gly Val
25                      30                  35

Phe Gly Thr Ala Tyr Leu Val Pro Arg His Leu Phe
                40                  45

Ala Glu Lys Tyr Asp Lys Ile Met Leu Asp Gly Arg
        50                  55              60

Ala Met Thr Asp Ser Asp Tyr Arg Val Phe Glu Phe
                65                  70

Glu Ile Lys Val Lys Gly Gln Asp Met Leu Ser Asp
            75                  80

Ala Ala Leu Met Val Leu His Arg Gly Asn Arg Val
85                      90                  95

Arg Asp Ile Thr Lys His Phe Arg Asp Thr Ala Arg
                100                 105

Met Lys Lys Gly Thr Pro Val Val Gly Val Val Asn
        110                 115                 120

Asn Ala Asp Val Gly Arg Leu Ile Phe Ser Gly Glu
                125                 130

Ala Leu Thr Tyr Lys Asp Ile Val Val Cys Met Asp
                135                 140

Gly Asp Thr Met Pro Ser Leu Phe Ala Tyr Lys Ala
145                 150                 155

Ala Thr Lys Ala Gly Tyr Cys Gly Gly Ala Val Leu
                160                 165

Ala Lys Asp Gly Ala Asp Thr Phe Ile Val Gly Thr
        170                 175                 180

His Ser Ala Gly Gly Asn Gly Val Gly Tyr Cys Ser
                    185                 190

Cys Val Ser Lys Ser Met Leu Leu Arg Met Lys Ala
            195                 200

His Val Asp Pro Glu Pro Gln His Glu
205                 210

(2) INFORMATION FOR SEQ ID NO:4:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:4:

Phe Arg Glu Arg Thr Leu Thr Gly Gln Arg Ala Cys
1               5                   10

Asn Asp Val Asn Ser Glu
            15

(2) INFORMATION FOR SEQ ID NO:5:

(i) SEQUENCE CHARACTERISTICS:
        (A) LENGTH: 18 amino acids

```
        (B) TYPE: amino acid
        (D) TOPOLOGY: linear (ii) MOLECULE TYPE: peptide (xi) SEQUENCE DESCRIPTION: SEQ ID NO:5:

Asn Pro Leu Glu Thr Ser Gly Ala Ser Thr Val Gly
1               5                   10

Phe Arg Glu Arg Thr Leu
            15

(2) INFORMATION FOR SEQ ID NO:6:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:6:

Ile Arg Glu Thr Arg Lys Arg Gln Lys Met Val Asp
1               5                   10

Asp Ala Val Asn Glu Tyr
            15

(2) INFORMATION FOR SEQ ID NO:7:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:7:

Ala Lys Ala Pro Val Val Lys Glu Gly Pro Tyr Glu
1               5                   10

Gly Pro Val Lys Lys Pro Val
            15

(2) INFORMATION FOR SEQ ID NO:8:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:8:

Ala Gly Pro Leu Glu Arg Gln Lys Pro Leu Lys Val
1               5                   10

Lys Ala Lys Ala Pro Val Val
            15

(2) INFORMATION FOR SEQ ID NO:9:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:9:
```

```
Lys Val Arg Ala Lys Leu Pro Gln Gln Glu Gly Pro
1               5                   10

Tyr Ala Gly Pro Leu Glu Arg
            15

(2) INFORMATION FOR SEQ ID NO:10:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:10:

Gly Pro Tyr Thr Gly Pro Leu Glu Arg Gln Arg Pro
1               5                   10

Leu Lys Val Arg Ala Lys Leu
            15

(2) INFORMATION FOR SEQ ID NO:11:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:11:

Val Gly Arg Leu Ile Phe Ser Gly Glu Ala Leu Thr
1               5                   10

Tyr Lys Asp Ile Val Val
            15

(2) INFORMATION FOR SEQ ID NO:12:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:12:

Thr Lys His Phe Arg Asp Thr Ala Arg Met Lys Lys
1               5                   10

Gly Thr Pro Val Val Gly Val
            15

(2) INFORMATION FOR SEQ ID NO:13:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:13:

Ser Gly Ala Pro Pro Thr Asp Leu Gln Lys Met Val
1               5                   10

Met Gly Asn Thr Lys Pro Val
            15
```

(2) INFORMATION FOR SEQ ID NO:14:

(i) SEQUENCE CHARACTERISTICS:
        (A) LENGTH: 66 amino acids
        (B) TYPE: amino acid
        (D) TOPOLOGY: linear (ii) MOLECULE TYPE: peptide (xi) SEQUENCE DESCRIPTION: SEQ ID NO:14:

```
Ile Arg Glu Thr Arg Lys Arg Gln Lys Met Val Asp
1               5                   10

Asp Ala Val Asn Glu Tyr Ile Glu Lys Ala Asn Ile
            15                  20

Thr Thr Asp Asp Thr Thr Leu Asp Glu Ala Glu Lys
25                  30                  35

Asn Pro Leu Glu Thr Ser Gly Ala Ser Thr Val Gly
            40                  45

Phe Arg Glu Arg Thr Leu Thr Gly Gln Arg Ala Cys
50                  55                  60

Asn Asp Val Asn Ser Glu
            65
```

(2) INFORMATION FOR SEQ ID NO:15:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:15:

```
Asn Pro Leu Glu Thr Ser Gly Ala Ser Thr Val Gly
1               5                   10

Phe Arg Glu Arg Thr Leu Thr Gly Gln Arg Ala Cys
            15                  20

Asn Asp Val Asn Ser Glu
25                  30
```

(2) INFORMATION FOR SEQ ID NO:16:

(i) SEQUENCE CHARACTERISTICS:
        (A) LENGTH: 58 amino acids
        (B) TYPE: amino acid
        (D) TOPOLOGY: linear (ii) MOLECULE TYPE: peptide (xi) SEQUENCE DESCRIPTION: SEQ ID NO:16:

```
Gly Pro Tyr Thr Gly Pro Leu Glu Arg Gln Arg Pro
1               5                   10

Leu Lys Val Arg Ala Lys Leu Pro Gln Gln Glu Gly
            15                  20

Pro Tyr Ala Gly Pro Leu Glu Arg Gln Lys Pro Leu
25                  30                  35

Lys Val Lys Ala Lys Ala Pro Val Val Lys Glu Gly
            40                  45

Pro Tyr Glu Gly Pro Val Lys Lys Pro Val
50                  55
```